(12) United States Patent
Jan

(10) Patent No.: US 9,126,181 B2
(45) Date of Patent: Sep. 8, 2015

(54) CATALYSTS FOR IMPROVED CUMENE PRODUCTION AND METHOD OF MAKING AND USING SAME

(71) Applicant: UOP LLC, Des Plaines, IL (US)

(72) Inventor: Deng-Yang Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/973,811

(22) Filed: Aug. 22, 2013

(65) Prior Publication Data

US 2013/0345045 A1      Dec. 26, 2013

Related U.S. Application Data

(62) Division of application No. 13/471,102, filed on May 14, 2012, now Pat. No. 8,524,966.

(51) Int. Cl.
| | |
|---|---|
| *B01J 29/06* | (2006.01) |
| *C07C 2/66* | (2006.01) |
| *B01J 29/70* | (2006.01) |
| *B01J 37/00* | (2006.01) |

(52) U.S. Cl.
CPC ........ *B01J 29/06* (2013.01); *B01J 29/70* (2013.01); *B01J 37/0009* (2013.01); *C07C 2/66* (2013.01); *B01J 2229/16* (2013.01); *B01J 2229/36* (2013.01); *B01J 2229/40* (2013.01); *B01J 2229/42* (2013.01); *C07C 2521/04* (2013.01); *C07C 2521/06* (2013.01); *C07C 2521/08* (2013.01); *C07C 2521/10* (2013.01); *C07C 2529/70* (2013.01)

(58) Field of Classification Search
USPC .................................. 502/60, 63, 64, 85, 86
See application file for complete search history.

(56) References Cited

U.S. PATENT DOCUMENTS

| | | | | |
|---|---|---|---|---|
| 5,378,671 | A * | 1/1995 | Keville et al. .................... | 502/64 |
| 5,500,109 | A * | 3/1996 | Keville et al. .............. | 208/111.3 |
| 5,681,789 | A * | 10/1997 | Saxton et al. .................... | 502/85 |
| 7,449,169 | B2 | 11/2008 | Corma Canos et al. | |
| 2004/0199036 | A1 | 10/2004 | Jan | |

FOREIGN PATENT DOCUMENTS

| | | |
|---|---|---|
| EP | 0873291 B1 | 1/2002 |
| SU | 245729 A1 | 11/1969 |
| WO | 2012051037 A2 | 4/2012 |

OTHER PUBLICATIONS

International Search Report for International Application No. PCT/US2013/038992, mailing date Aug. 29, 2013.

* cited by examiner

*Primary Examiner* — Elizabeth Wood

(57) ABSTRACT

An aromatic alkylation catalyst is presented. The aromatic alkylation catalyst comprised a zeolite, an inorganic oxide, and silanol functional groups of less than about 0.65 area/mg on the surface of the catalyst.

8 Claims, No Drawings

CATALYSTS FOR IMPROVED CUMENE PRODUCTION AND METHOD OF MAKING AND USING SAME

CROSS-REFERENCE TO RELATED APPLICATION

This application is a Division of prior application Ser. No. 13/471,102 which was filed on May 14, 2012 now U.S. Pat. No. 8,524,966, which is incorporated herein by reference in its entirety.

FIELD OF THE INVENTION

The disclosure relates in general to the formation of isopropylbenzene (cumene) through catalytic alkylation of benzene. In certain embodiments, the disclosure relates to a zeolitic alkylation catalyst with a low level of surface silanol functional groups having enhanced cumene selectivity.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al, as well as structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversions, which can take place on outside surfaces as well as on internal surfaces within the pore.

One such hydrocarbon conversion process includes the catalytic monoalkylation of benzene with propylene to produce isopropylbenzene (cumene) using the zeolitic catalyst designated UZM-8. While the primary product is isopropylbenzene, quantities of polyalkylated benzene variants are also produced in small quantities. These polyalkylated variants can be recovered via fractionation and trans-alkylation but are undesirable due to the additional utility cost and yield loss during the trans-alkylation process. As such, technology to increase the selectivity of the catalytic alkylation to isopropylbenzene over the polyalkylated variants is desired.

SUMMARY OF THE INVENTION

In one embodiment, an alkylation catalyst is presented. The alkylation catalyst comprises a zeolite, an inorganic oxide, and silanol functional groups of less than about 0.65 area/mg on the surface of the catalyst.

In another embodiment, a method for preparing an alkylation catalyst is presented. The method comprises providing a zeolite, washing the zeolite with water, forming an extrudate from the zeolite and an inorganic oxide, heating the extrudate in a first calcining step to produce a calcined catalyst, exposing the calcined catalyst to an ion exchange solution comprising ammonium ions to produce an ion exchanged catalyst, and heating the ion exchanged catalyst in a second calcining step to produce an alkylation catalyst.

In yet another embodiment, a method for producing cumene is presented. The method comprises contacting an alkylation catalyst with a stream of benzene and propylene. The alkylation catalyst comprises a zeolite, an inorganic oxide, and silanol functional groups of less than about 0.65 area/mg on a surface of the alkylation catalyst.

DETAILED DESCRIPTION OF PREFERRED EMBODIMENTS

The catalytic compositions used in the processes of the current invention comprise Applicant's cumene alkylation catalyst. Applicant's catalyst is a microporous crystalline zeolite. In one embodiment, the catalyst is prepared in an alkali-free reaction medium in which only one or more organoammonium species are used as structure directing agents. Applicant's catalyst is a modified UZM-8 catalyst, which has a composition in the as-synthesized form and on an anhydrous basis expressed by empirical formula (1).

$$R_r^{p+}Al_{1-x}E_xSi_yO_z \qquad (1)$$

In various embodiments, R is at least one organoammonium cation selected from the group consisting of protonated amines, protonated diamines, quaternary ammonium ions, diquaternary ammonium ions, protonated alkanolamines and quaternized alkanolammonium ions.

In one embodiment the organoammonium cations are non-cyclic. In one embodiment the organoammonium cations do not comprise a cyclic group as one substituent. In one embodiment, the organoammonium cations comprise at least one methyl group as a substitute. In one embodiment, the organoammonium cations comprise at least two methyl groups as substituents. In certain embodiments, the cations are selected from the group consisting of diethyldimethylammonium (DEDMA), ethyltrimethylammonium (ETMA), hexamethonium (HM) and mixtures thereof.

The ratio of R to (Al+E) is represented by "r" which varies from about 0.05 to about 5. The value of "p" which is the weighted average valence of R varies from about 1 to about 2. The ratio of Si to (Al+E) in Applicant's zeolite catalyst is represented by "y" which varies from about 6.5 to about 35. E is an element which is tetrahedrally coordinated and present in the framework. In certain embodiments, E is selected from the group consisting of gallium, iron, chromium, indium and boron. The mole fraction of E is represented by "x" and has a value from about 0 to about 0.5, while "z" is the mole ratio of O to (Al+E) and is given by equation (2).

$$z = (r \cdot p + 3 + 4 \cdot y)/2 \qquad (2)$$

The zeolites can also be prepared using both organoammonium cations and alkali and/or alkaline earth cations as structure directing agents. As in the alkali-free case above, the same organoammonium cations can be used here. Alkali or alkaline earth cations are observed to speed up the crystallization of the zeolite, often when present in amounts less than 0.05 $M^+$/Si. For the alkali and/or alkaline earth metal containing systems, the microporous crystalline zeolite has a composition in the as-synthesized form and on an anhydrous basis expressed by empirical formula (3).

$$M_m^{n+}R_r^{p+}Al_{1-x}E_xSi_yO_z \qquad (3)$$

M is at least one exchangeable cation. In certain embodiments, M is selected from the group consisting of alkali and alkaline earth metals. In various embodiments, M comprises lithium, sodium, potassium, rubidium, cesium, calcium, strontium, barium, or mixtures thereof. In certain embodiments, R is selected from the group consisting of DEDMA, ETMA, HM, and mixtures thereof.

The value of "m" which is the ratio of M to (Al+E) varies from about 0.01 to about 2. The value of "n" which is the weighted average valence of M varies from about 1 to about 2. The ratio of R to (Al+E) is represented by "r" which varies from 0.05 to about 5. The value of "p" which is the weighted average valence of R varies from about 1 to about 2. The ratio of Si to (Al+E) is represented by "y" which varies from about 6.5 to about 35. E is an element which is tetrahedrally coordinated and present in the framework. In certain embodiments, E is selected from the group consisting of gallium, iron, chromium, indium and boron.

The mole fraction of E is represented by "x" and has a value from about 0 to about 0.5, while "z" is the mole ratio of O to (Al+E) and is given by equation (4).

$$z = (m \cdot n + r \cdot p + 3 + 4 \cdot y)/2 \qquad (4)$$

In some embodiments, where M consists of a single metal, the weighted average valence is the valence of the metal, i.e. +1 or +2. In other embodiments, where M consists of a plurality of metals, the total metal amount is represented by (5) and the weighted average valence "n" is given by equation (6).

$$M_m^{n+} = M_{m1}^{(n1)+} + M_{m2}^{(n2)+} + M_{m3}^{(n3)+} + \ldots \qquad (5)$$

$$n = \frac{m_1 \cdot n_1 + m_2 \cdot n_2 + m_3 \cdot n_3 + \ldots}{m_1 + m_2 + m_3 \ldots} \qquad (6)$$

Similarly when only one R organic cation is present, the weighted average valence is the valence of the single R cation, i.e., +1 or +2. When more than one R cation is present, the total amount of R is given by equation (7).

$$R_r^{p+} = R_{r1}^{(p1)+} + R_{r2}^{(p2)+} + R_{r3}^{(p3)+} \qquad (7)$$

and the weighted average valence "p" is given by the equation (8).

$$p = \frac{p_1 \cdot r_1 + p_2 \cdot r_2 + p_3 \cdot r_3 + \ldots}{r_1 + r_2 + r_3 \ldots} \qquad (8)$$

In various embodiments, the microporous crystalline zeolites are prepared by a hydrothermal crystallization of a reaction mixture prepared by combining reactive sources of R, aluminum, and silicon. In various embodiments, the microporous crystalline zeolites are prepared by a hydrothermal crystallization of a reaction mixture prepared by combining reactive sources of R, aluminum, silicon, and M. In various embodiments, the microporous crystalline zeolites are prepared by a hydrothermal crystallization of a reaction mixture prepared by combining reactive sources of R, aluminum, silicon, and E. In various embodiments, the microporous crystalline zeolites are prepared by a hydrothermal crystallization of a reaction mixture prepared by combining reactive sources of R, aluminum, silicon, M and E.

In various embodiments, the source of aluminum is selected from the group consisting of aluminum alkoxides, precipitated aluminas, aluminum metal, sodium aluminate, organoammonium aluminates, aluminum salts, and alumina sols. Specific examples of aluminum alkoxides include, but are not limited to aluminum ortho sec-butoxide, and aluminum ortho isopropoxide. Other sources of aluminum may be used in other embodiments.

In various embodiments, the source of silica is selected from the group consisting of tetraethylorthosilicate, colloidal silica, precipitated silica, alkali silicates, and organoammonium silicates. Other sources of silica may be used in other embodiments.

A special reagent consisting of an organoammonium aluminosilicate solution can also serve as the simultaneous source of Al, Si, and R.

In various embodiments, the source of E is selected from the group consisting of alkali borates, boric acid, precipitated gallium oxyhydroxide, gallium sulfate, ferric sulfate, ferric chloride, chromium nitrate, and indium chloride. Other sources of E may be used in other embodiments.

In various embodiments, the source of M is selected from the group consisting of halide salts, nitrate salts, sulfate salts, acetate salts, and hydroxides of the respective alkali or alkaline earth metals. Other sources of M may be used in other embodiments.

In certain embodiments, R can be introduced as an organoammonium cation or an amine. In the embodiments where R is a quaternary ammonium cation or a quaternized alkanolammonium cation, the source of R may be selected from the group consisting of hydroxide, chloride, bromide, iodide and fluoride compounds. Specific examples of such sources of R, include without limitation, DEDMA hydroxide, ETMA hydroxide, tetramethylammonium hydroxide, tetraethylammonium hydroxide, hexamethonium hydroxide, tetrapropylammonium hydroxide, methyltriethylammonium hydroxide, tetramethylammonium chloride, and choline chloride. In some embodiments, R may be introduced as an amine, diamine, or alkanolamine that subsequently hydrolyzes to form an organoammonium cation. In some embodiments, the source of R is selected from the group consisting of N,N,N,N-tetramethyl-1,6-hexanediamine, triethylamine, and triethanolamine. In some embodiments, the source of R is selected from the group consisting of ETMAOH, DEDMAOH, and HM(OH)$_2$.

The reaction mixture containing reactive sources of the desired components can be described in terms of molar ratios of the oxides by formula (9).

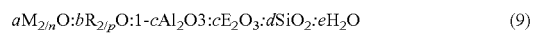

$$aM_{2/n}O:bR_{2/p}O:1-cAl_2O_3:cE_2O_3:dSiO_2:eH_2O \qquad (9)$$

In various embodiments, "a" varies from 0 to about 25, "b" varies from about 1.5 to about 80, "c" varies from 0 to 1.0, "d" varies from about 10 to about 100, and "e" varies from about 100 to about 15000. If alkoxides are used, it is preferred to include a distillation or evaporative step to remove the alcohol hydrolysis products.

The reaction mixture is reacted at a temperature of about 85° C. to about 225° C. and preferably from about 125° C. to about 150° C. for a period of about 1 day to about 28 days and preferably for a time of about 5 days to about 14 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C.

In some embodiments, the zeolite is synthesized from a homogenous solution. Soluble aluminosilicate precursors condense during digestion to form extremely small crystallites that have a great deal of external surface area and short diffusion paths within the pores of the crystallites. This can affect both adsorption and catalytic properties of the material.

As-synthesized, the zeolite material will contain some of the charge balancing cations in its pores. In the case of syntheses from alkali or alkaline earth metal-containing reaction mixtures, some of these cations may be exchangeable cations that can be exchanged for other cations. In the case of organoammonium cations, they can be removed by heating under controlled conditions. In the cases where the zeolite is prepared in an alkali-free system, the organoammonium cations are best removed by controlled calcination, thus generating the acid form of the zeolite without any intervening ion-exchange steps. On the other hand, it may sometimes be possible to remove a portion of the organoammonium via ion exchange. In a special case of ion exchange, the ammonium form of the zeolite catalyst may be generated via calcination of the organoammonium form of the zeolite in an ammonia atmosphere.

The properties of the compositions described above can be modified after formation of the zeolite material by removing some of the aluminum atoms from the framework and optionally inserting silicon atoms. Treating processes include, without limitation, treatment with a fluorosilicate solution or slurry, extraction with a weak, strong or complexing acid, etc. In carrying out these dealumination treatments, the particular form of the zeolite is not critical, but can have a bearing on the final product especially with regard to the extent of dealumination.

Thus, the zeolite catalyst can be used as synthesized or can be ion exchanged to provide a different cation form. In this respect, the starting zeolite can be described by empirical formula (10).

$$M'^{n'+}_{m'} R^{p+}_{r'} Al_{(1-x)} E_x Si_y O_{z'} \qquad (10)$$

R, x, y, and E are as described above and m' has a value from about 0 to about 7.0, M' is a cation selected from the group consisting of alkali metals, alkaline earth metals, rare earth metals, hydrogen ion, ammonium ion, and mixtures thereof, n' is the weighted average valence of M' and varies from about 1 to about 3, r' has a value from about 0 to about 7.0, r'+m'>0, and p is the weighted average valence of R and varies from about +1 to about +2. The value of z' is given by the formula (11).

$$z' = (m' \cdot n' + r' \cdot p + 3 + 4 \cdot y)/2 \qquad (11)$$

The zeolite catalyst is used as a catalyst or a catalyst support for a number of hydrocarbon conversion processes known in the art. These include cracking, hydrocracking, alkylation of both aromatics and isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, methanation and syngas shift process.

In many hydrocarbon conversion processes, the zeolite is mixed with a binder for convenient formation of catalyst particles in a proportion of about 5 to 95 mass % zeolite and 5 to 95 mass-% binder, with the zeolite preferably comprising from about 10 to 90 mass-% of the composite. The binder should preferably be porous, have a surface area of about 5 to about 800 m$^2$/g, and be relatively refractory to the conditions utilized in the hydrocarbon conversion process. In various embodiments, the binders comprise an inorganic oxide. In various embodiments, the binders comprise, without limitation, alumina, titania, zirconia, zinc oxide, magnesia, boria, silica-alumina, silica-magnesia, chromia-alumina, alumina-boria, silica-zirconia, silica, silica gel, and clays. In various embodiments, the binders comprise amorphous silica and alumina, including gamma-, eta-, and theta-alumina.

In various embodiments, the zeolite with or without a binder are formed into various shapes such as pills, pellets, extrudates, spheres, etc. In some embodiments, the extrudates are prepared by conventional means, involving mixing the zeolite either before or after adding metallic components, with the binder and a suitable peptizing agent to form a homogeneous dough or thick paste having the correct moisture content to allow for the formation of extrudates with acceptable integrity to withstand direct calcination. The dough is then extruded through a die to give the shaped extrudate. A multitude of different extrudate shapes are possible, including, but not limited to, cylinders, cloverleaf, dumbbell and symmetrical and asymmetrical polylobes. In some embodiments, the extrudates are shaped to any desired form, such as spheres, by any means known to the art.

In some embodiments, the zeolite can be formed into a sphere by the oil-drop method described in U.S. Pat. No. 2,620,314, which is incorporated by reference. The method involves dropping a mixture of zeolite, and for example, alumina sol, and a gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50-200° C. and subjected to a calcination procedure at a temperature of about 450-700° C. for a period of about 1 to about 20 hours. This treatment effects conversion of the hydrogel to the corresponding alumina matrix.

One of the uses of the formed zeolite catalyst has been to catalyze alkylation of aromatic compounds. In these applications, an aromatic compound is reacted with an olefin using the zeolitic catalyst. In various embodiments, the olefins comprises from 2 to about 20 carbon atoms. In various embodiments, the olefins comprise branched olefins or linear olefins and either terminal or internal olefins. In various embodiments, the olefins comprise ethylene, propylene, and olefins which are known as "detergent range olefins," or a combination thereof "Detergent range olefins" are linear olefins containing from 6 up through about 20 carbon atoms which have either internal or terminal double bonds. In certain embodiments, the olefins comprise linear olefins containing from 8 to about 16 carbon atoms. In certain embodiments, the olefins comprise linear olefins containing from 10 to about 14 carbon atoms.

In various embodiments, the zeolitic catalyst is used to catalyze alkylation of benzene, naphthalene, anthracene, phenanthrene, and substituted derivatives thereof. For example, alkylation of benzene is illustrated by (15), where benzene (12) is reacted with propylene (13) to form cumene (isopropylbenzene) (14).

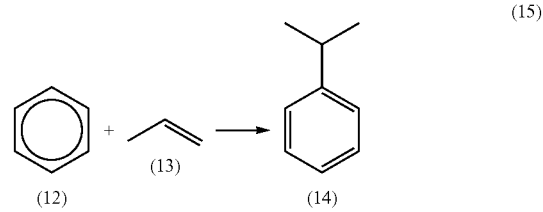

(15)

(12) + (13) → (14)

In other embodiments, the catalyst has been used to catalyze alkylation of other aromatic compounds capable of alkylation by an olefinic compound. In various embodiments, such aromatic compounds have one or more substituents selected from the group consisting of alkyl groups (having from 1 to about 20 carbon atoms), hydroxyl groups, and alkoxy groups whose alkyl group also contains from 1 up to 20 carbon atoms. In embodiments where the substituent is an alkyl or alkoxy group, a phenyl group can also can be substituted on the alkyl chain. In some embodiments, such aromatic compounds comprise biphenyl, toluene, xylene, ethylbenzene, propylbenzene, butylbenzene, pentylbenzene, hexylbenzene, heptylbenzene, octylbenzene, phenol, cresol, anisole, ethoxy-, propoxy-, butoxy-, pentoxy-, hexoxybenzene, and combinations thereof.

The particular conditions for the monoalkylation reaction depend upon the aromatic compound and the olefin used. In various embodiments, the reaction is conducted under at least partial liquid phase conditions. Therefore, the reaction pressure is adjusted to maintain the olefin at least partially dissolved in the liquid phase. For higher olefins, the reaction may be conducted at autogenous pressure. As a practical matter, the pressure normally is in the range between about 200 and about 1,000 psig (1480-6997 kPa) but usually is in a range between about 300-600 psig (2170-4238 kPa). The alkylation of aromatic compounds with the olefins in the C2-C20 range can be carried out at a temperature of about 60° C. to about 400° C., and in some embodiments, from about 90° C. to about 250° C., for a time sufficient to form the desired product. In some embodiments, the alkylation of benzene with ethylene is carried out at temperatures of about 200° C. to about 250° C. and the alkylation of benzene by propylene at a temperature of about 90° C. to about 200° C. The ratio of aromatic compound to olefin will depend upon the degree of selective monoalkylation desired as well as the relative costs of the aromatic and olefinic components of the reaction mixture. For alkylation of benzene by propylene, benzene-to-olefin ratios may be as low as about 1 and as high as about 10, with a ratio of 1.5-8 being preferred. Where benzene is alkylated with ethylene, a benzene-to-olefin ratio is, in one embodiment, between about 1:1 and 8:1. For detergent range olefins of C6-C20, a benzene-to-olefin ratio of between 3:1 up to as high as 30:1 is generally sufficient to ensure the desired monoalkylation selectivity, with a range between about 5:1 and about 20:1 being preferred.

In some instances, the zeolitic catalyst has been used to catalyze transalkylation. Transalkylation involves intermolecular transfer of an alkyl group on one aromatic nucleus to a second aromatic nucleus. Transalkylation involves the transfer of one or more alkyl groups of a polyalkylated aromatic compound to a nonalkylated aromatic compound, and is exemplified by reaction of diisopropylbenzene (16) with benzene (17) to give two molecules of cumene (18) via reaction (19).

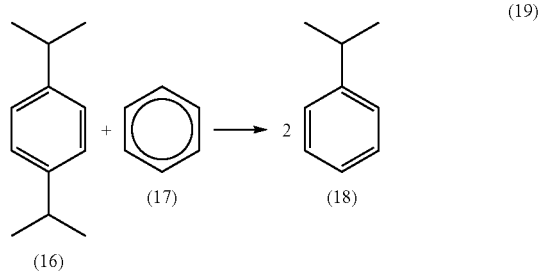

Transalkylation is often utilized to add to the selectivity of a desired selective monoalkylation by reacting the polyalkylates invariably formed during alkylation with nonalkylated aromatic to form additional monoalkylated products. For the purposes of this process, the polyalkylated aromatic compounds are those formed in the alkylation of aromatic compounds with olefins as described above, and the nonalkylated aromatic compounds are benzene, naphthalene, anthracene, and phenanthrene. The reaction conditions for transalkylation are similar to those for alkylation, with temperatures being in the range of about 100° C. to about 250° C., pressures in the range of about 100 to about 750 psig (about 791 kPa to about 5272 kPa), and the molar ratio of unalkylated aromatic to polyalkylated aromatic in the range from about 1 to about 10. Examples of polyalkylated aromatics that may be reacted with, for example, benzene as the nonalkylated aromatic, include without limitation, diethylbenzene, diisopropylbenzene, dibutylbenzene, triethylbenzene, triisopropylbenzene and tetraethylbenzene.

In processes where a UZM-8 catalyst has been used to catalyze alkylation of benzene with propylene to produce cumene, Applicant has observed that a decrease in the occurrence of silanol groups on the surface of the catalyst result in higher cumene selectivity. It is believed that a high occurrence of surface silanol groups result in an increased production of undesirable polyalkylated benzene variants. As such, catalysts with a low occurrence of surface silanol functional groups are desired to increase cumene selectivity.

In order to increase the selectivity of the UZM-8 catalyst as applied to the catalytic monoalkylation of aromatics, Applicant has developed a new zeolite catalyst with low levels of surface silanol groups. When Applicant's catalyst is used in cumene production processes involving benzene monoalkylation under conventional operating conditions, Applicant's catalyst results in increased selectivity to cumene over the polyalkylated benzene variants as compared to prior UZM-8 catalysts used in aromatic monoalkylation reactions.

Applicant has found that the ratio of silicon to aluminum moieties in the zeolite is increased to minimize the presence of surface silanol groups. Increasing the $Si/Al_2$ ratio results in a porous zeolite catalyst with a low level of surface silanol functional groups. The surface silanol groups (Si—OH) are decreased while maintaining the active surface framework acid sites (Al—OH—Si moieties) responsible for catalyzing the alkylation reaction.

In various embodiments, zeolite is flushed with an excessive amount of water before being incorporate into the catalyst. The resulting catalyst has a lower level of surface silanol groups, while maintaining the active surface framework acid sites (Si—OH—Al moieties) responsible for the alkylation reaction.

In various embodiments, the aluminum moieties used to prepare Applicants' zeolite catalyst is selected from the group consisting of aluminum alkoxides, precipitated aluminas, aluminum metal, sodium aluminate, organoammonium aluminates, aluminum salts, and alumina sols. In one embodiment, the aluminum moiety is alumina.

Without wishing to be bound by any particular theory, the increase in the silica to aluminum ratio in the zeolite appears to reduce the aluminum available for alumination reactions, which result in the formation of surface silanol groups. In various embodiments, the $Si/Al_2$ molar ratio is between about 15 and about 35. In various embodiments the $Si/Al_2$ molar ratio is between about 18 and about 30.

The following Examples are presented to further illustrate to persons skilled in the art how to make and use Applicants' catalyst. These Examples are not intended as a limitation, however, upon the scope of Applicant's invention.

Example 1

In a large beaker 160.16 grams of diethyldimethylammonium hydroxide was added to 1006.69 grams de-ionized water, followed by 2.79 grams of 50 wt % NaOH solution. Next, 51.48 grams of liquid sodium aluminate was added slowly and stirred for 20 minutes. Then, 178.89 grams of $SiO_2$ (sold in commerce as Ultrasil) was slowly added to the gel and stirred for 20 minutes. Next, 24 grams of zeolite seed was added to the gel and stirred for an additional 20 minutes. The gel was then transferred to a 2-liter stirred reactor and heated to 160° C. in 2 hours, and crystallized for 115 hours. After digestion, the material was filtered and washed with de-ionized water and dried at 100° C. The elemental analysis by inductively coupled plasma-atomic emission spectroscopy (ICP-AES) was Si=41.4 wt %, Al=3.94 wt %, Na=2.23 wt % corresponding to a $Si/Al_2$ molar ratio of 20.3, and 7.4 weight percent C, 2.4 weight percent H and 1.4 weight percent N. A portion of the zeolite was calcined at 600° C., ammonium exchanged and then calcined at 500° C. to obtain a BET surface area of 464 $m^2/g$, a total pore volume of 1.26 cc/g, and a micropore volume of 0.101 cc/g by $N_2$ adsorption isotherm. Surface area and pore volume are calculated using nitrogen partial pressure $p/p_O$ data points ranging from about 0.03 to about 0.30 using the BET (Brunauer-Emmett-Teller) model method using nitrogen adsorption technique as described in ASTM D4365-95, Standard Test Method for Determining Micropore Volume and Zeolite Area of a Catalyst, and in the article by S. Brunauer et al., J. Am. Chem. Soc., 60(2), 309-319 (1938).

The zeolite was dried at 100° C. for 12 hours and then exchanged using ammonium nitrate followed by water wash to lower $Na_2O$ below 500 wppm. It was then shaped by extruding into pellets of cylindrical extrudate of 1/16" diameter containing 70 mass % zeolite and 30 mass % alumina on a volatile free basis. The formed catalyst was dried at 110° C. for 2 hours, and calcined in a box oven at about 600° C. for about 1 hour in flowing air.

Example 2

Following the same preparation as Example 1 up to the drying step, the zeolite was dried at 100° C. for 12 hours and extruded into pellets of cylindrical extrudate of 1/16" diameter containing 70 mass % zeolite and 30 mass % alumina on a volatile free basis. The formed catalyst was dried at 110° C. for 2 hours, and calcined in a box oven at about 540° C. for about 1 hour in flowing air. The calcined extrudate was ammonium exchanged using an ammonium nitrate solution of about 10 wt % at about 65° C. for 2 hours to lower the sodium content below 500 wppm as $Na_2O$ on a volatile free basis and dried at about 100° C. for 2 hours to produce a dried, ion exchanged extrudate. The ion exchange dry base is then activated at 450° C. in a box oven in a flowing air for 2 hours. The final catalyst contained 0.09 wt % total nitrogen as determined by method ASTM 5291.

Example 3

In a washing step, 50 grams of zeolite prepared according to Example 1 was added to 2000 ml of de-ionized $H_2O$ at 60° C. $H_2O$ was decanted after about one hour of contact. The procedure was repeated 4 times. The resulting zeolite showed 42.0 wt % Si, 4.05 wt % Al and 1.3 wt % Na on a volatile free basis, and C=7.4%, H=2.4% and N=1.4 wt % on an as received basis. A portion of the zeolite was calcined at 600° C., ammonium exchanged and then calcined at 500° C. to obtain a BET surface area of 508 $m^2/g$, a total pore volume of 1.31 cc/g, and a micropore volume of 0.119 cc/g by $N_2$ adsorption isotherm.

The zeolite was then dried at 100° C. for 12 hours and extruded into pellets of cylindrical extrudate of 1/16" diameter containing 70 mass % zeolite and 30 mass % alumina on a volatile free basis. The formed catalyst was dried at 110° C. for 2 hours, and calcined in a box oven at 600° C. in flowing air for 2 hours. The calcined extrudate was ammonium exchanged using an ammonium nitrate solution of about 10 wt % at about 65° C. for 2 hours to lower the sodium content below 500 wppm as $Na_2O$ on a volatile free basis and dried at about 100° C. for 2 hours to produce a dried, ion exchanged extrudate. The ion exchange dry base is then activated at 425° C. in a box oven in a flowing air for 2 hours. The final catalyst comprises 0.13 wt % total nitrogen as determined by method ASTM 5291.

Example 4

In a large makeup tank 7124 grams of diethyldimethylammonium hydroxide (20%) was added, followed by 375 grams of aluminum tri-sec-butoxide (97%). The resulting solution was stirred for 10 minutes. 4124 grams of de-ionized water was then added to the solution, followed by the 30-minutes slow addition of 2000 grams of 89% $SiO_2$. Next a solution of 75 grams of NaBr dissolved in 1000 grams of de-ionized water was added to another solution made up of 273 grams of tetramethylammonium bromide in 1000 grams of de-ionized water. The resulting solution of tetramethylammonium bromide and sodium bromide was then added to the silica-alumina solution containing diethyldimethylammonium. Thereafter, 160 grams of zeolite seed with a $Si/Al_2$ molar ratio of 27 is added. The resulting gel was then pumped to the 5-gallon reactor, followed by rinsing the makeup tank with 1000 grams of de-ionized water and pumping the rinse to the 5-gallon reactor. The final gel was crystallized at 150° C. for 100 hours with an agitation at 150 rpm. After digestion the material was centrifuged at 10,000 rpm for 10 minutes using an excess amount of de-ionized $H_2O$. The centrifuge with excess de-ionized $H_2O$ was repeated 5 times and dried at 50° C. The resulting zeolite showed 43.1 wt % Si, 3.1 wt % Al and 0.37 wt % Na on a volatile free basis, and C=5.5%, H=7.7% and N=1.3 wt % on an as received basis. A portion of the zeolite was calcined at 600° C., ammonium exchanged and then calcined at 500° C. to obtain a BET surface area of 373 $m^2/g$, a total pore volume of 0.57 cc/g, and a micropore volume of 0.130 cc/g by $N_2$ adsorption isotherm.

The zeolite was then extruded into pellets of cylindrical extrudate of 1/16" diameter containing 70 mass % zeolite and 30 mass % alumina on a volatile free basis. The formed catalyst was dried at 110° C. for 2 hours, and calcined in a box oven at 600° C. in flowing air for 2 hours. In different embodiments, the calcinating occurs between 300° C. to about 650° C. for between about 10 minutes to about 20 hours. The calcined extrudate was ammonium exchanged using an ammonium nitrate solution of about 10 wt % at about 65° C. for 2 hours to lower the sodium content below 500 wppm as $Na_2O$ on a volatile free basis and dried at about 100° C. for 2 hours to produce a dried, ion exchanged extrudate. The ion exchange dry base is then activated by calcinating at 425° C. in a box oven with flowing air for 2 hours. In different embodiments, the calcinating occurs between about 300° C. and about 650° C. for between about 10 minutes to about 20 hours. The final catalyst contains 0.12 wt % total nitrogen as determined by method ASTM 5291.

The infrared measurement is performed by first pretreating the sample at 500° C. in flowing helium for 2 hours. The sample is cooled to room temperature to take the spectrum. Pyridine adsorption was performed at 150° C. for one hour followed by discrete desorptions at 150° C., 300° C. & 450° C. with the spectra taken at room temperature followed each discrete desorption. The species from wave numbers of 3700 to 3764 cm-1 are assigned as surface silanol functional groups specifically, various terminal silanol. The areas under this specific range is integrated and normalized to area per milligram.

To test the performance of Applicant's catalyst, 25 grams of the catalyst is mixed with quartz sand to fill the interstitial voids to ensure proper flow distribution before loaded into a 7/8" ID standard steel reactor. The catalyst is dried down in flowing benzene pretreated using 3 A dryer at 200° C. for 12 hours. After the drydown, the recycled benzene is introduced followed by propylene. The test condition consists of a benzene to propylene molar ratio targeted at 2.0, a product effluent to combined fresh feed ratio of 7.4 on a weight basis, propylene weight hourly space velocity of 1.04 $hr^{-1}$, an inlet temperature of 115° C. and an outlet pressure of 500 psig (3549 kPa). The product effluent is monitored by on-line GC. The catalyst activity is measured by the fraction of catalyst bed required to reach maximal temperature, i.e., the less catalyst required to attain the maximal temperature, the higher the catalyst activity. The selectivity to cumene is calculated based on the moles of cumene out of total moles of cumene and diisopropylbenzene.

The results in Table 1 below show that cumene selectivity is improved when a zeolite with a $Si/Al_2$ molar ratio of 20 is subjected to an extended water wash (i.e., flush). A zeolite with a $Si/Al_2$ molar ratio of 27 also shows high cumene selectivity, when washed extensively during the zeolite workup. It is believed that the extended water wash and/or the combination of increased $Si/Al_2$ molar ratio and extended water wash lowers the silanol functional group, contributing to improved cumene selectivity.

TABLE 1

| Example | Si—OH (area/mg, 3764-3700 cm-1, before Pyridine adsorption) | Cumene/(Cumene + DIPB) (molar selectivity) |
| --- | --- | --- |
| Example 1 | 0.796 | 79.6 |
| Example 2 | 0.687 | 82.3 |
| Example 3 | 0.481 | 85.2 |
| Example 4 | 0.574 | 86.1 |

In certain embodiments, a catalyst comprising an inorganic oxide and a zeolite with a $Si/Al_2$ molar ratio of about 20 to about 30 is washed at temperatures ranging from about 10° C. to 99° C.

In various embodiments, the amount of surface silanol functional groups on the catalyst is less than 0.77 area/mg (where the area is derived by integrating the absorbance peak between the wavelengths of $3700 \text{ cm}^{-1}$ to $3764 \text{ cm}^{-1}$ in the infrared spectrum). In various embodiments, the amount of surface silanol functional groups on the catalyst is less than 0.65 area/mg. In various embodiments, the amount of surface silanol functional groups on the catalyst is less than 0.49 area/mg.

In one embodiment, the catalyst is then placed in a stream of benzene and propylene to form cumene, where the stream comprises a liquid. In various embodiments, the environment in which the benzene and propylene stream is brought in contact with the catalyst comprises a temperature of between about 60° C. to about 200° C., a pressure of between about 200 psig (1480 kPa) and about 1000 psig (6997 kPa), and with a liquid hourly space velocity for the stream of benzene and propylene of about 0.1 $hr^{-1}$ to about 10 $hr^{-1}$.

The described features, structures, or characteristics of the invention may be combined in any suitable manner in one or more embodiments. In the above description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention. In other words, the present invention may be embodied in other specific forms without departing from its spirit or essential characteristics. The described implementations are to be considered in all respects only as illustrative and not restrictive. The scope of the invention should, therefore, be determined not with reference to the above description, but instead should be determined with reference to the pending claims along with their full scope or equivalents, and all changes which come within the meaning and range of equivalency of the claims are to be embraced within their full scope.

What is claimed is:

1. An aromatic alkylation catalyst, comprising:
   a UZM-8;
   an inorganic oxide; and
   silanol functional groups of less than about 0.65 area/mg on a surface of said UZM-8.

2. The aromatic alkylation catalyst of claim 1, wherein said inorganic oxide is selected from the group consisting of silica, alumina, magnesia, zirconia, and combinations thereof.

3. The aromatic alkylation catalyst of claim 1, wherein said UZM-8 has a $Si/Al_2$ molar ratio between about 18 to about 30.

4. The aromatic alkylation catalyst of claim 1, prepared by the steps of:
   providing a UZM-8;
   washing said UZM-8 with water;
   forming an extrudate from said UZM-8 and an inorganic oxide;
   heating said extrudate in a first calcining step to produce a calcined catalyst;
   exposing the calcined catalyst to an ion exchange solution comprising ammonium ions to produce an ion exchanged catalyst; and
   heating the ion exchanged catalyst in a second calcining step to produce an alkylation catalyst.

5. The aromatic alkylation catalyst of claim 4, wherein said heating said extrudate comprises a temperature of between about 300° C. to about 650° C. for between about 10 minutes to about 20 hours.

6. The aromatic alkylation catalyst of claim 5, wherein said heating said ion exchange catalyst comprises a temperature of between about 300° C. to about 650° C. for between about 10 minutes to about 20 hours.

7. The aromatic alkylation catalyst of claim 6, wherein said inorganic oxide is selected from the group consisting of silica, alumina, magnesia, zirconia, and combinations thereof.

8. The aromatic alkylation catalyst of claim 7, wherein said UZM-8 has a $Si/Al_2$ molar ratio between about 18 to about 30.

* * * * *